United States Patent
Cho et al.

(10) Patent No.: US 11,096,597 B2
(45) Date of Patent: Aug. 24, 2021

(54) METHOD FOR MEASURING BLOOD PRESSURE INFORMATION AND A BLOOD PRESSURE MEASURING APPARATUS USING THE SAME

(71) Applicant: KOREA ADVANCED INSTITUTE OF SCIENCE AND TECHNOLOGY, Daejeon (KR)

(72) Inventors: Seong Hwan Cho, Daejeon (KR); Dong Hee Kim, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 385 days.

(21) Appl. No.: 16/142,023

(22) Filed: Sep. 26, 2018

(65) Prior Publication Data

US 2019/0099090 A1 Apr. 4, 2019

(30) Foreign Application Priority Data

Sep. 29, 2017 (KR) .......................... 10-2017-0127529

(51) Int. Cl.
*A61B 5/021* (2006.01)
*A61B 5/352* (2021.01)
*A61B 5/024* (2006.01)

(52) U.S. Cl.
CPC ...... *A61B 5/02116* (2013.01); *A61B 5/02125* (2013.01); *A61B 5/352* (2021.01); *A61B 5/02416* (2013.01); *A61B 2560/0209* (2013.01)

(58) Field of Classification Search
CPC .............. A61B 5/0456; A61B 5/02416; A61B 5/14552; A61B 2560/0209
See application file for complete search history.

(56) References Cited

U.S. PATENT DOCUMENTS

2012/0203077 A1* 8/2012 He ....................... A61B 5/6815
600/301
2017/0128020 A1   5/2017 Olivier et al.
2018/0279898 A1* 10/2018 Pamula .............. A61B 5/02416

FOREIGN PATENT DOCUMENTS

KR   10-2010-0124409 A   11/2010
WO   WO-2018002541 A1 *  1/2018 ......... A61B 5/02416

OTHER PUBLICATIONS

English translation of WO-2018002541-A1 (EPO: Dec. 2, 2020). (Year: 2018).*

* cited by examiner

*Primary Examiner* — Amanda Lauritzen Moher
*Assistant Examiner* — Delia M. Appiah Mensah
(74) *Attorney, Agent, or Firm* — Novick, Kim & Lee, PLLC; Sang Ho Lee (57) ABSTRACT

Provided are a method for measuring blood pressure information and a blood pressure measuring apparatus using the same as which improve the battery efficiency, the possibility of portability, and easy measurement of the device equipped with the blood pressure measurement function by both minimizing power consumption and optimizing signal delivery system in the measurement of the blood pressure information using ECG and PPG. The blood pressure measuring apparatus includes a first peak detection unit for detecting a first peak information from an electrocardiographic signal of a patient obtained from an electrocardiogram detection unit; a second peak detection unit for detecting a second peak information from an optical pulse waveform detection signal of the patient obtained from an optical pulse wave detection unit; and a control unit for calculating a pulse wave arrival time information indicating a blood pressure information depending on the first peak information and the second peak information.

6 Claims, 4 Drawing Sheets

METHOD FOR MEASURING BLOOD PRESSURE INFORMATION AND A BLOOD PRESSURE MEASURING APPARATUS USING THE SAME

CROSS-REFERENCE TO RELATED APPLICATION

This application claims the priority to Korean patent application No. 10-2017-0127529 filed on Sep. 29, 2017, the disclosure of which is incorporated herein by reference.

TECHNICAL FIELD

The present invention is a method for measuring blood pressure information and an apparatus for measuring blood pressure using the same as, and more particularly to the method for measuring blood pressure information and the apparatus for measuring blood pressure using the same as, which measure the blood pressure information using ECG and PPG.

BACKGROUND ART

In general, blood pressure is an important biological index including cardiac output that of the amount of blood ejected for one minute in the human heart, the elasticity of blood vessels, information about the patient's physiological changes.

Medical method for detecting the blood pressure has an invasive blood pressure detection method for continuously detecting the blood pressure by inserting a catheter into a blood vessel, and a noninvasive blood pressure detection method for detecting the blood pressure by sensing sound or vibration as applying pressure using a blood pressure-cuff.

However, these methods have still limit that it was difficult to both hand carry detection equipment and to accurately measure the blood pressure since the detection is available only in a hospital or the like.

Meanwhile, the relationship between blood pressure and pulse transit time (PTT) has been proven recently, a method of estimating blood pressure information by detecting the PTT has been proposed. Accordingly, both not invasive and a cuff-less blood pressure measuring device has been proposed in this field.

However, these PTT detection may be obtained following conditions that the electrocardiogram (ECG) of a patient should be detected, an optical pulse wave, that is photoplethysmo-graphic signal (PPG signal) of the patient is detected, and the pulse transit time (PTT) of the patient is analyzed based on the detected ECG value and the detected PPG signal, and then the blood pressure value of the patient may be detected by applying the analysis results into a regression equation.

However, the portability has not improved since the power consumption of the detection equipment for ECG detection and PPG measurement has been excessively consumed.

In particular, detection modules of ECG and PPG must be activated at the same time to simultaneously measure ECG and PPG for PTT analysis, the power consumption can be consumed by more than simply operating only each module, thereby having difficulty for power management.

Currently, mounting of such ECG or PPG measuring functions is attempted in wearable devices and various portable devices such as a smart watch. But, if ECG and PPG are continuously measured, the battery would quickly consume, thereby dropping the measuring devices of efficiency. The problem of power consumption of simultaneous measurement of ECG and PPG for blood pressure measurement is becoming more prominent in such wearable devices.

In addition, it has still problem to the wearable method and the measuring method for simultaneous measurement of ECG and PPG. For example, the pulse waves should be measured while two or more electrodes are connected to both ends of the human body for simultaneous measurement of ECG and PPG with a specific posture, since unconscious measurement is almost impossible in the specific posture.

For these reasons, the blood pressure measuring functions and the possibility of applications for portable healthcare devices have been limited, thus making difficult environment to research and develop products.

DISCLOSURE

Technical Problem

The present invention has been made to solve the above problems, an object of the present invention is to provide a method for measuring blood pressure information and a blood pressure measuring apparatus using the same as which improve the battery efficiency, the possibility of portability, and easy measurement of the device equipped with the blood pressure measurement function by both minimizing power consumption and optimizing signal delivery system in the measurement of the blood pressure information using ECG and PPG.

Technical Solution

To achieve the object of the present invention, there is provided to a blood pressure measuring apparatus, comprises a first peak detection unit for detecting a first peak information from an electrocardiographic detection signal of a patient obtained from an electrocardiogram detection unit; a second peak detection unit for detecting a second peak information from an optical pulse waveform detection signal of the patient obtained from an optical pulse wave detection unit; and a control unit for calculating a pulse wave arrival time information indicating a blood pressure information depending on the first peak information and the second peak information.

Also, there is provided to a blood pressure measuring circuit, comprises a first peak detection block for obtaining a first peak information from an electrocardiographic detection signal of a patient obtained from an electrocardiogram detection unit; a second peak detection block for detecting a second peak information from an optical pulse waveform detection signal of the patient obtained from an optical pulse wave detection unit; and a counter block for calculating a pulse wave arrival time information indicating a blood pressure information depending on the first peak information and the second peak information.

In addition, there is provided to a method for measuring a blood pressure, comprises the steps of: obtaining a first peak information from an electrocardiographic signal of a patient obtained from an electrocardiogram detection unit; detecting a second peak information from an optical pulse waveform detection signal of the patient obtained from an optical pulse wave detection unit; and calculating a pulse wave arrival time information indicating a blood pressure information depending on the first peak information and the second peak information.

Advantageous Effects

According to the present invention, there are provided a method for measuring blood pressure information and an blood pressure measuring apparatus using the same as which improve the battery efficiency, the possibility of portability, and easy measurement of the device equipped with the blood pressure measurement function by both minimizing power consumption and optimizing signal delivery system in the measurement of the blood pressure information using ECG and PPG according to the calculation of the pulse wave arrival time information based on first peak information of an electrocardiogram signal and second peak formation of an optical pulse wave detection signal.

According to the present invention, in particular, the power sources of both an electrocardiogram detection unit and an optical pulse wave detection unit may be alternately controlled in accordance with the first peak information and the second peak information, thereby minimizing the power consumption thereof.

BEST MODE

Content of below illustrates only a principle of the present invention. Therefore, those skilled in the art will invention to a variety of devices that are included in the scope of this concept, although clearly described or implementing the principles of the present invention, have not been shown herein invention. Further, all the conditional terms and embodiments listed herein, for example, are as a general rule, and only to that understanding the concept of the present invention clearly intended, be understood that not limited to this manner specifically enumerated embodiments and conditions do.

In addition, not only the principles, viewpoints and embodiments of the invention all the description listing the particular embodiments are to be understood to be intended to include structural and functional equivalents of such locations. In addition, it is to be understood as including equivalents such waters all devices invented to make, as well as equivalents now known or that is independent of the equivalent structures will be developed in the future to perform the same function.

Thus, for example, block diagrams of the present specification are to be understood as representing a conceptual viewpoint of an exemplary circuit that embodies the principles of the invention. Similarly, all the flowcharts, state conversion degree, the pseudo-code, etc. are understood to represent a variety of processes regardless of whether the computer can substantially represent the readable medium there is clearly shown a computer or processor, and executed by a computer or processor, it should be.

Functions of the various elements shown in the Figures, including functional blocks labeled as a processor or a similar concept can be provided through the use of dedicated hardware as well as hardware that has the capability of executing software in association with appropriate software. When provided by a processor, the functions may be provided by a single dedicated processor, single shared processor, or a plurality of individual processors, some of which may be shared.

The processor, control, or the explicit use of the term to be presented in a similar concept is to be construed by the hardware has the capability of executing software exclusive recited is not being, ROM for storing a digital signal processor (DSP) hardware, software, without limitation, (ROM), it is to be understood as comprising a random access memory (RAM) and nonvolatile memory implicitly. It can not contain other hardware in tolerance.

In the claims of this specification, the component expressed as a means for performing a function described in the detailed description include, for example, any type of software, including performing the function circuit combinations or firmware/microcode in the element such as was intended to include all methods for performing a function, it is combined with appropriate circuitry for executing the software for performing the functions. The present invention as defined by such claims are functions provided by the various listed means are coupled are bonded to the way that the claims require any means that can provide the function also equivalent to those identified from the specification it should be understood that.

The aforementioned objects, features and advantages will become more apparent from the following description in conjunction with the accompanying drawings, a self-technical features of the present invention one of ordinary skill in the art thus can be easily There will be. Further, the detailed description of the known art related to the invention In the following description of the present invention will be omitted and a detailed description on the case that are determined to unnecessarily obscure the subject matter of the present invention.

Hereinafter, a preferred embodiment of the present invention will be described in detail with reference to the accompanying drawings.

Figure 1:
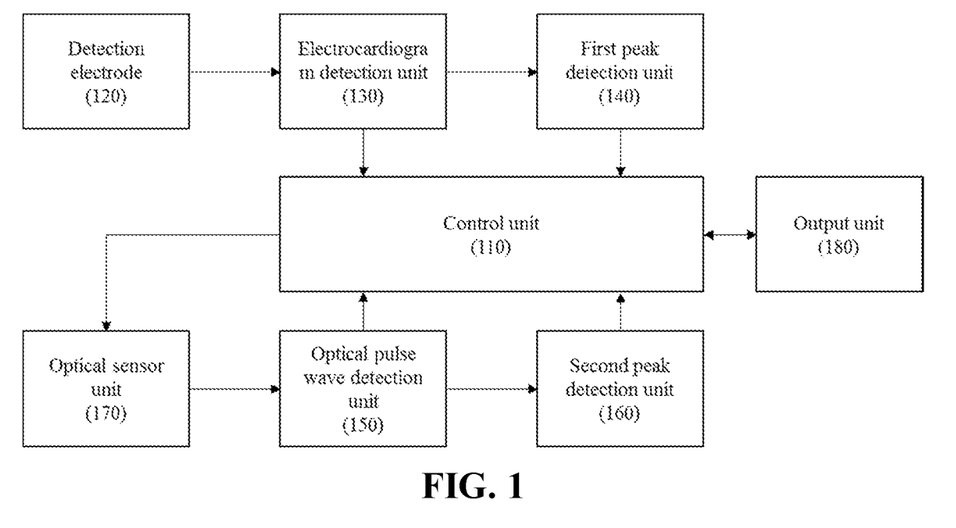
FIG. 1 is a block diagram for explaining a blood pressure measuring apparatus according to an embodiment of the present invention.

FIG. 1 is a block diagram for explaining a blood pressure measuring apparatus according to an embodiment of the present invention.

The blood pressure measuring apparatus 100 according to the embodiment of the present invention may be configured as an independent blood pressure measuring apparatus or may be applied to a portable terminal in a modularized manner. Also, the blood pressure measuring apparatus 100 may further include an input unit, a storage unit, a display unit, or a communication unit, as not shown, which are generally configured in portable terminals in the embodiment of the present invention. For example, the control unit 110 may be implemented as a means for measuring blood information based on an electrocardiographic and an optical pulse wave detection through a conventional control unit of a mobile communication terminal, thereby enabling accurate measurement of the blood pressure information.

Accordingly, the blood pressure measuring apparatus 100 according to the embodiment of the present invention, referring to FIG. 1, includes a control unit 110, a detection electrode 120, an electrocardiogram detection unit 130, a first peak detection unit 140, an optical pulse wave detection unit 150, a second peak detection unit 160, an optical sensor unit 170 and an output unit 180.

First, the detection electrode 120 detects an electrical signal for detecting an e electrocardiogram (ECG) of a patient, the detected signal may transmit to the electrocardiogram detection unit 130.

The electrocardiogram detection unit 130 detects the electrocardiogram from the detected electrical signal, and transmits the detected electrocardiogram value to the control unit 110. Here, the electrocardiogram detection method may use one of known electrocardiogram measuring methods, while the electrocardiogram measurement method is not limited to the present invention.

Further, the electrocardiogram detection unit 130 may obtain the electrocardiographic waveform information detected from the detection electrode 120 in electrocardiographic detection process. And the ECG waveform information may transmit to the first peak detection unit 140.

The first peak detection unit 140 may obtain the first peak information indicating a point or a period at which the peak is generated from the electrocardiographic waveform information, and may output the first peak information to the control unit 110.

Here, the first peak information may include R-peak information using the characteristic of the R wave from the characteristics of the electrocardiogram signal. In other words, the electrocardiogram detection unit 130 may detect waveform information including P, Q, R, S, and T waves, which is an electrocardiogram waveform that reflects the electrical activation phase of the heart, But it may provide the blood pressure measuring apparatus 100 that enables accurate measurement while minimizing power consumption by measuring a pulse wave arrival time (PAT) using the first peak detection of the P wave and the second peak detection information of the pulse wave of the optical pulse wave detection unit 150.

First, the electrocardiogram detection unit 130 may provide the electrocardiographic waveform information of the R wave including the potential of a R peak, the variableness refractory of the myocardium, and the kurtosis information between neighboring waveforms to the first peak detection unit 140. While the first peak detection unit 140 detects both the generation potential and the temporal position information of the R peak corresponding to the highest potential from the electrocardiographic waveform information of the R wave, and the detected potential information or the temporal information may constitute the first peak information or may transmit to the control unit 110.

On the other hand, the optical pulse wave detection unit 150 may detect the optical pulse waveform information from the optical sensing signal received from the optical sensor unit 170, and may transmit the detected optical pulse waveform information to the control unit 110 and the second peak detection unit 160.

For example, the optical sensor unit 170 may radiate the optical signal modulated by the specific frequency to the human body, and may sense the optical signal reflected from the human body and may transmit to the optical pulse wave detection unit 150.

The optical pulse wave detection unit 150 may detect the optical pulse wave signal by demodulating the reflected optical signal, and may transmit the optical pulse waveform information obtained from the optical pulse wave signal to the control unit 110 and the second peak detection unit 160.

The second peak detection unit 160 detects the second peak point information from the optical pulse waveform information, and may transmit the detected point information to the control unit 110. Here, the second peak point information may correspond to a maximum slope point of the optical pulse waveform information. Also, the second peak point information may be detected from the differential value of the optical pulse waveform, while a point having a maximum differential value may be corresponded to the second peak point.

Accordingly, the control unit 110 may calculate the electrocardiographic waveform information detected from the electrocardiogram detection unit 130 and the pulse wave arrival time (PAT) for measuring the blood pressure information from the optical pulse waveform information detected by the optical pulse wave detection unit 150, and may obtain the blood pressure information from the calculated PAT information, and may output the obtained blood pressure information through the output unit 180 with communication, screen, or voice signals.

Here, the pulse wave arrival time (PAT) may include a time period from the R peak point corresponding to the first peak point of the electrocardiographic waveform information to the maximum slope point corresponding to the second peak point of the optical pulse waveform information. More specifically, the PAT representing the blood pressure information may be a time period that combines the pre-ejection period (PEP) and the pulse transit time (PTT) of the human heart.

In particular, the blood pressure measuring apparatus may obtain useful blood pressure information using only partial waveforms for each period corresponding to the first peak and the second peak from the waveform period, while the more precise measurement is required to detect the PTT as the previous pulse wave transmission time, That is, the electric power and calculation efficiency may be improved since the PAT measurement does not require complete ECG and PPG waveforms of all the periods, and it can be implemented in such a manner that the blood pressure measurement apparatus may be attached to a more free position of the human body to unconsciously measure.

For example, the blood pressure measuring apparatus 100 is implemented in the form of an arm-band for PAT measurement by integrating the detection electrode 120 and the optical sensor unit 170 each other to be wrapped around a specific part of the human body, such as an arm or a leg. As a result, the blood pressure information may be measured without taking any specific action or attitude.

Therefore, the control unit 110 according to the embodiment of the present invention may measure the blood pressure information using the partial waveform information for each time period corresponding to the PAT of each electrocardiogram detection unit 130 and the optical pulse wave detection unit 150 corresponding to the first peak information and the second peak information respectively, and may output the measurement result corresponding thereto to the output unit 180.

In addition, the control unit 110 alternately performs power application of the electrocardiogram detection unit 130 and the optical pulse wave detection unit 150 depending on the peak information detected from the first peak detection unit 140 and the second peak detection unit 160, so that each detection unit controls only in a time period for obtaining the partial waveform information. This explanation of thereof will be described in detail later.

Figure 2:
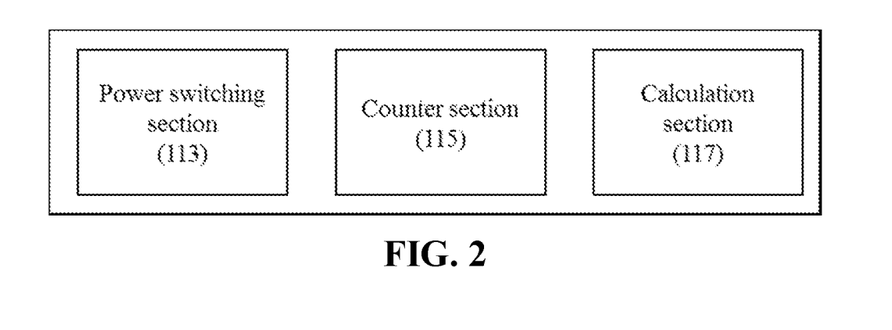
FIG. 2 is a block diagram for detailly explaining a control unit according to an embodiment of the present invention.

FIG. 2 is a block diagram for detailly explaining the control unit according to the embodiment of the present invention.

First, referring to FIG. 2, the control unit 110 according to the embodiment of the present invention includes a power switching section 113, a counter section 115, and a calculation section 111.

The power switching unit 113 may alternately control the power applied to the electrocardiogram detection unit 130 and the optical pulse wave detection unit 150 by using the first peak information and the second peak information received from the first peak detection unit 140 and the second peak detection unit 160.

The counter section 115 may measure the time information between the first peak information and the second peak information and may transmit the measured time information to the calculation section 111.

Accordingly, the calculation section 111 may calculate the pulse wave arrival time (PAT) depending on the time period between the first peak information and the second peak information, and the calculated information may be processed with the blood pressure information, or output through the output unit 180 as raw data formation.

Figure 3:
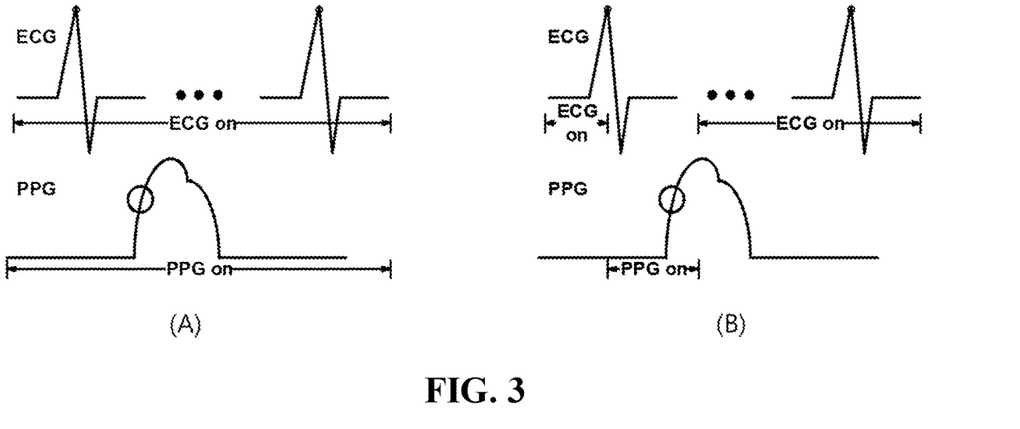
FIG. 3 is a comparative diagram for explaining an alternating control of the power according to the peak period of an electrocardiogram detection unit and a pulse wave detection unit according to an embodiment of the present invention.
Figure 4:
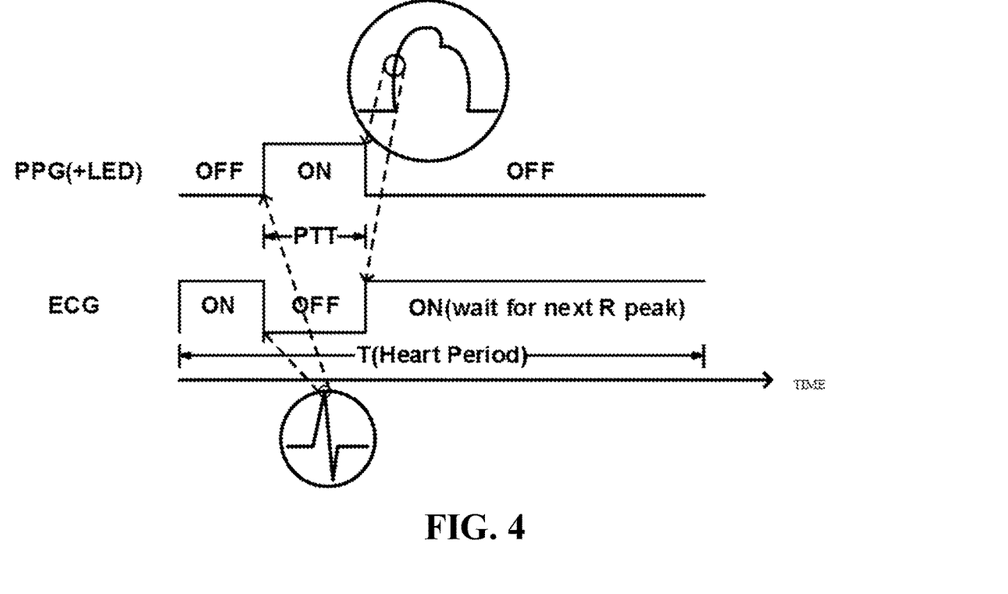
FIG. 4 shows a control signal variation by a time period determined depending on a peak period according to an embodiment of the present invention.

FIG. 3 is a comparative diagram for explaining an alternating control of the power according to the peak period of an electrocardiogram detection unit and an pulse wave detection unit according to the embodiment of the present invention, and FIG. 4 shows a control signal variation by a time period determined depending on a peak period according to the embodiment of the present invention.

FIG. 3 (A) shows a power application state when electrocardiogram and optical pulse wave detection are performed in a conventional detection device, it may be known that the power application state is always maintained power on state to obtain all kinds of the waveforms from the ECG detection unit and the optical pulse wave (PPG) detection unit.

However, as shown in FIG. 3 (B) in the embodiment of the present invention, the electrocardiogram detection unit 130 controls the power application to be powered on state only during the first peak period in which the first peak information of the electrocardiogram detection unit 130 can be measured by controlling the power switching section 113. In addition, the power switching section 113 controls the power application to be powered off state in the remaining period, thereby minimizing the power consumption.

On the other hand, the control unit 110 may control the power application of the optical pulse wave detection unit 150 to be powered on state only during the second peak period in which the second peak information of the optical pulse wave detection unit 150 may be measured, and control the power application to be powered off state in the remaining period, thereby minimizing the power consumption.

As shown in FIG. 4, the electrocardiogram detection unit 130 and the optical pulse wave detection unit 150 is controlled to be alternately operated in power on state within each necessary detection period for each peak information, and operated in power off state during a period other than the detection period, thereby minimizing the power consumption, and heat generation, battery efficiency and portability may be improved, respectively.

For example, the power switching section 113 may operate to be powered off the electrocardiogram detection unit 130 when the first peak information (ECG R-Peak) is detected in a state in which ECG read-out period of the electrocardiogram detection unit 130 having the relatively low power consumption is powered on state, and the power switching section controls to be powered on the optical pulse wave detection unit 150 and controls the counter section 115 for PAT measurement, simultaneously.

Thereafter, the power switching unit 113 may operate to be powered off the LED of the optical sensor unit 170 at the second peak point where a sharp maximum rising edge is detected in the PPG read-out period of the optical pulse wave detection unit 150. Accordingly, the power switching unit 113 operate to be powered on again the ECG read-out period of the electrocardiogram detection unit 130 and to be powered off the counter unit 115.

Accordingly, the counter unit 115 may output the time counter corresponding to the actual PAT, the calculation unit 111 may calculate and output the blood pressure information according to the output time counter.

Particularly, it still has the problem that the battery is most consumed by an optical element such as LEDs corresponding to the optical sensor unit 170. Therefore, according to the embodiment of the present invention, the power switching unit 113 may operate to be powered on state only during the second peak period corresponding to the second peak detection, and operate to be powered off state in the remaining period, thereby maximizing the power efficiency, where the power is corresponding to the optical sensor unit 170 of the optical pulse wave detection unit 150.

Figure 5:
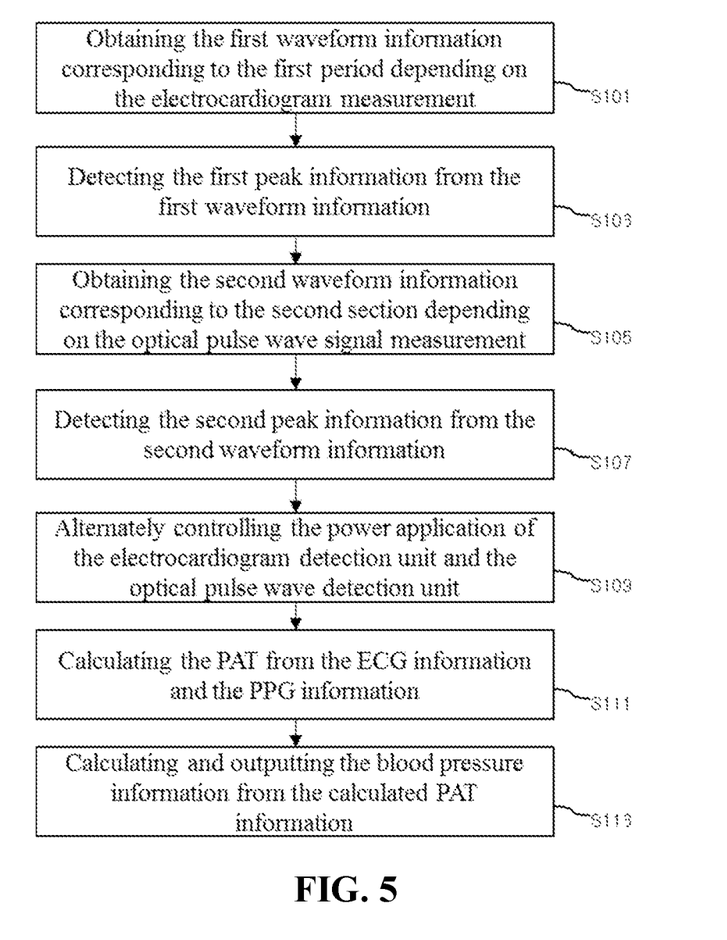
FIG. 5 is a flowchart for explaining a blood pressure measuring method according to an embodiment of the present invention.

FIG. 5 is a flowchart for explaining the blood pressure measuring method according to the embodiment of the present invention.

Referring to FIG. 5, the blood pressure measuring apparatus 100 according to the embodiment of the present invention obtains the first waveform information corresponding to the first period depending on the electrocardiogram measurement of the electrocardiogram detection section 130 (performed at Step S101).

Then, the blood pressure measuring apparatus 100 detects the first peak information from the first waveform information by the first peak detection unit 140 (performed at Step S103).

Here, the first period may be a period including the first peak, and the electrocardiogram detecting section 130 may be controlled to be powered on state only during the first peak section, and may be controlled to be powered off state during the remaining period.

In addition, the blood pressure measuring apparatus 100 obtains the second waveform information corresponding to the second section depending on the optical pulse wave signal measurement received from the optical sensor unit 170 by the optical pulse wave detection unit 150 (performed at Step S105).

Then, the blood pressure measuring apparatus 100 detects the second peak information from the second waveform information by the second peak detection unit 160 (performed at Step S107).

Here, the second section may be a period including the second peak, the electrocardiogram detection unit 130 may be controlled to be powered on state only during the second peak period, and may be controlled to be powered off state during the remaining period.

For this control, the blood pressure measuring apparatus 100 may be alternately control the power application of the electrocardiogram detection unit 130 and the optical pulse wave detection unit 150 based on the first peak information and the second peak information by calculating the control unit 110 (performed at Step S109).

Accordingly, the control unit 110 of the blood pressure measuring apparatus 100 may calculate the PAT from the ECG information measured in the first period and the PPG information measured in the second period (performed at Step S111), and calculate the blood pressure information from the calculated PAT information, and output the blood pressure information through the output unit 180 (performed at Step S113).

Thus, the present invention allows that cuff-less blood pressure measurement using PAT becomes possible, the charging frequency can be reduced due to improvement of the power efficiency, and unconsciously continuous measurement may be enabled to reduce the power consumption.

In particular, the control unit 110 may control to be alternately On/Off state using the characteristics of the ECG and PPG waveforms according to the electrocardiogram detection unit 130 and the optical pulse wave detection unit 150. Accordingly, it is possible to obtain a complementary power consumption reduction in the form of variable control so that the power supply is mutually fed back, since the ECG controls the PPG, while the PPG controls the ECG.

Figure 6:
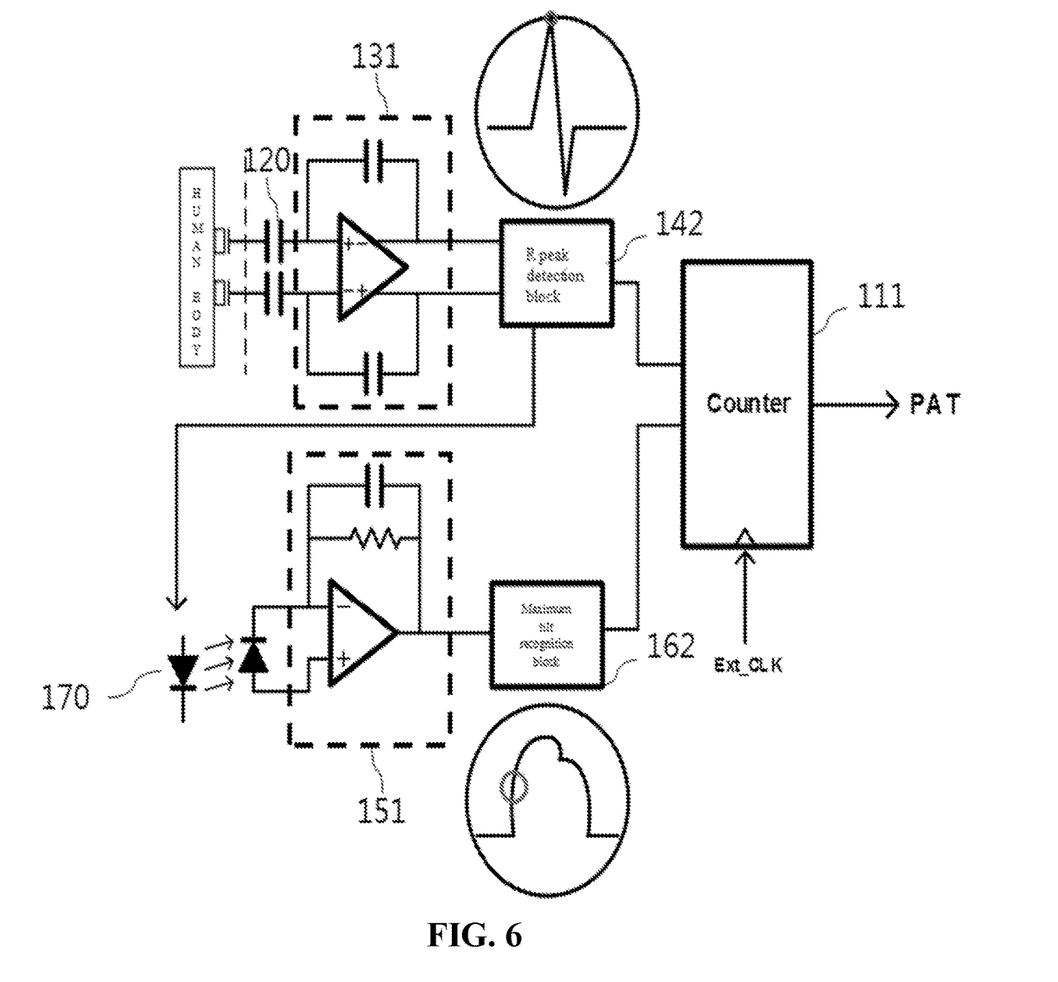
FIG. 6 is a circuit diagram for explaining a blood pressure measuring circuit of a blood pressure measurement apparatus according to an embodiment of the present invention.

FIG. 6 is a circuit diagram for explaining a blood pressure measuring circuit of the blood pressure measurement apparatus according to the embodiment of the present invention.

Referring to FIG. 6, the detection electrode 120 of the blood pressure measuring apparatus 100 according to the embodiment of the present invention may include one or more capacitors in contact with the human body, the electrocardiogram detection unit 130 may include an amplification circuit 131 for amplifying and detecting a signal detected from the detection electrode 120. The first peak detection unit 140 connected to the electrocardiogram detection unit 130 may be configured as an R peak detection block 142, or a digital block for recognizing the R peak, or may be constituted by a differentiator and a comparator circuit In addition, the optical pulse wave detection unit 150 may include a transimpedance amplifier circuit 151 for detecting the PPG pulse from the optical sensor unit 170. The second peak detection unit 160 connected to the optical pulse wave detection unit 150 may include a maximum tilt recognition block 162 for detecting the maximum tilt, or a differentiator and a comparator circuit.

Accordingly, the time period between the detected first peak signal and the second peak signal may be counted by the counter unit 115, the pulse wave arrival time (PAT) may be calculated and output depending on the counted time period, thereby enabling measurement of the blood pressure information.

According to such the circuit configuration, when the ECG and the PPG are simultaneously measured, the blood pressure measuring apparatus of the present invention may variably control to be mutually fed back the optical pulse wave detection unit 150 and the LED driver of the optical sensor unit 170 which consume a lot of electric power depending on the PEAK information of the ECG waveform and the PPG waveform, thereby minimizing the power consumption by controlling to be powered on state only when the PPG measurement is required. In addition, the blood pressure measuring apparatus of the present invention may lead to a very large power reduction effect compared to conventional ECG and PPG measuring devices. As an example, when the conventional measuring vice consumes 20 mW, the blood pressure measuring apparatus of the present invention may consume 1 mW. Thus, if mass-production and commercialization of the blood pressure measuring apparatus will be achieved, the electric power may be reduced to a large difference.

According to the present invention, it is possible to automatically set the appropriate virtual machine server in the cloud computing system that is the policy to be applied to the virtual machine after the virtual machine is created, IP address or domain information. In addition, in a policy it can be set for automatic virtual machine to a non-manual, and can handle the process efficiently in generating the virtual machine on the same template or on a large scale deployment.

The present invention can also be embodied as computer readable code on a computer-readable recording medium. The computer-readable recording medium includes all kinds of recording devices in which data that can be read by a computer system. Examples of the computer-readable recording medium include ROM, RAM, CD-ROM, a magnetic tape, a floppy disc, optical data storage devices, and it is implemented in the form of carrier waves (such as data transmission through the Internet) It includes. Further, the computer-readable recording medium is distributed over network coupled computer systems so that the computer readable code is stored and executed in a distributed fashion. Then, the functional (functional) programs, codes, and code segments for accomplishing the present invention can be easily construed by programmers skilled in the art to which the invention pertains.

In addition, more than the been shown and described a preferred embodiment of the invention, the invention is not limited to the embodiment of the above-described particular, technology pertaining the art without departing from the subject matter of the present invention claimed in the claims field in the embodiment and various modifications are possible as well as by those of ordinary skill, this modified embodiment would should not be understood individually from the technical spirit or prospect of the present invention.

What is claimed is:

1. A blood pressure measuring apparatus, comprising:
  a first peak detection circuit configured to detect a first peak information from an electrocardiographic signal of a patient obtained from an electrocardiogram detection circuit;
  a second peak detection circuit configured to detect a second peak information from an optical pulse waveform signal of the patient obtained from an optical pulse wave detection circuit; and
  a control circuit configured to calculate a pulse wave arrival time information indicating a blood pressure information based on the first peak information and the second peak information,
  wherein the control circuit includes a power switching circuit configured to control power applied to the electrocardiogram detection circuit and the optical pulse wave detection circuit to operate only one of the electrocardiogram detection circuit and the optical pulse wave detection circuit during a predetermined time period for obtaining a waveform detected only in the predetermined time period,
  wherein the power switching circuit is controlled to apply power such that only the optical pulse wave detection circuit is ON during a first time period from a detected time point of the first peak information to a detected time point of the second peak information, and
  wherein the power switching circuit is controlled to apply power such that only the electrocardiogram detection unit is ON during a second time period from a detected time point of the second peak information to a detected time point of the first peak information.

2. The blood pressure measuring apparatus according to claim 1, wherein the pulse wave arrival time information is calculated from a counted time period from a first point corresponding to the first peak information of the electrocardiographic waveform to a second point corresponding to the second peak information of the optical pulse waveform.

3. The blood pressure measuring apparatus according to claim 1, wherein the first peak information indicates a point or position of a R peak corresponding to the highest potential of a R signal waveform detected from the electrocardiographic detection circuit.

4. The blood pressure measuring apparatus according to claim 1, wherein the second peak information indicates a maximum point on a slope of the optical pulse waveform signal detected from the optical pulse wave detection circuit.

5. The blood pressure measuring apparatus according to claim 1, wherein the pulse wave arrival time information is obtained from a first period of a waveform corresponding to the first peak information of the electrocardiogram signal and a second period of a waveform corresponding to the second peak information of the optical pulse waveform signal.

6. A method for measuring a blood pressure, comprising:
    obtaining a first peak information from an electrocardiographic signal of a patient obtained from an electrocardiogram detection circuit;
    detecting a second peak information from an optical pulse waveform signal of the patient obtained from an optical pulse wave detection circuit; and
    calculating a pulse wave arrival time information indicating a blood pressure information based on the first peak information and the second pear information, wherein the control circuit includes a power switching circuit configured to control a power applied to the electrocardiogram detection circuit and the optical pulse wave detection circuit to operate only one of the electrocardiogram detection circuit and the optical pulse wave detection circuit during a predetermined time period for obtaining a waveform detected only in the predetermined time period, wherein the power switching circuit is controlled to apply power such that only the optical pulse wave detection circuit is ON during a first time period from a detected time point of the first peak information to a detected time point of the second peak information, and wherein the power switching circuit is controlled to apply power such that only the electrocardiogram detection unit is ON during a second time period from a detected time point of the second peak information to a detected time point of the first peak information.

* * * * *